United States Patent [19]
Ingram

[11] Patent Number: 5,919,460
[45] Date of Patent: Jul. 6, 1999

[54] COMPOSITION FOR ADMINISTRATION TO PATIENTS WITH CHRONIC FATIGUE SYNDROME AND ACQUIRED IMMUNE DEFICIENCY SYNDROME

[76] Inventor: Teresa J. Ingram, 4315 Spinks Creek La., Spring, Tex. 77388

[21] Appl. No.: 09/014,972

[22] Filed: Jan. 28, 1998

Related U.S. Application Data

[63] Continuation of application No. PCT/US96/12840, Jul. 29, 1996
[60] Provisional application No. 60/003,218, Aug. 2, 1995, abandoned.

[51] Int. Cl.⁶ .................................................. A61K 35/78
[52] U.S. Cl. ......................................... 424/195.1; 514/885
[58] Field of Search ........................... 424/195.1; 514/885

[56] References Cited

U.S. PATENT DOCUMENTS

| | | | |
|---|---|---|---|
| 4,059,695 | 11/1977 | Hirosaki et al. | 424/195.1 |
| 5,332,579 | 7/1994 | Umdenstock | 424/639 |
| 5,466,453 | 11/1995 | Uchida et al. | 424/195.1 |

*Primary Examiner*—Leon B. Lankford, Jr.
*Assistant Examiner*—Christopher R. Tate
*Attorney, Agent, or Firm*—Michael A. Sanzo; Vinson & Elkins L.L.P.

[57] ABSTRACT

The present invention is directed to a composition that can be used in alleviating symptoms associated with chronic fatigue syndrome or acquired immune deficiency syndrome. The composition is derived from the herbs Chimaphila umbellate, Apocynum andro-saemifolium, Symphytum officianale, and Equisetum hyemale. In addition, the invention is directed to a method of treating patients using this composition.

6 Claims, No Drawings

5,919,460

COMPOSITION FOR ADMINISTRATION TO PATIENTS WITH CHRONIC FATIGUE SYNDROME AND ACQUIRED IMMUNE DEFICIENCY SYNDROME

CROSS REFERENCE TO RELATED APPLICATIONS

The present application is a continuation of international application PCT/US96/12840, filed Jul. 29, 1996, which claims priority to U.S. application Ser. No. 60/003,218, filed Aug. 2, 1995 (now abandoned).

FIELD OF THE INVENTION

This invention relates to methods of treatment of the symptoms of Chronic Fatigue Syndrome (CFS), also known as Chronic Fatigue Immune Dysfunction Syndrome (CFIDS), and Acquired Immune Deficiency Syndrome (AIDS), and compositions useful in the performance of such methods. In addition, the invention relates to therapies and compositions for the treatment of symptoms associated with *Mycoplasma fermentans* infections.

BACKGROUND OF THE INVENTION

CFS is characterized by an abrupt onset of flu-like symptoms and persistent fatigue. Other symptoms include musculoskeletal pain; abnormal sleep patterns; neuropsychiatric symptoms such as headaches, blurred vision, dizziness, forgetfulness, excessive irritability, inability to concentrate, and depression; low grade fever; pharyngitis; swollen lymph nodes and weight loss. Many patients also have immunologic abnormalities. See Anthony L. Komaroff, *Clinical Presentation and Evaluation of Fatigue and Chronic Fatigue Syndrome* in Chronic Fatigue Syndrome 61, 70–71 (Stephen E. Straus, ed., 1994).

In 1990 researchers estimated that there were somewhere between three and five million cases of CFS in the United States (Cowley, G. Hager, M., Nadine, J., Chronic Fatigue Syndrome, A Debilitating Disease Afflicts Millions-And the Cause is Still a Mystery, Newsweek, Nov. 12, 1990). An accurate assessment is complicated by the lack of a reliable test for CFS and the fact that many CFS patients are misdiagnosed as having cancer, multiple sclerosis, depression, or Lyme disease.

A human retrovirus family, including human immunodeficiency virus type 1 (HIV-1) and human immunodeficiency virus type 2 (HIV-2), is accepted by most scientists as the primary infectious agent causing AIDS. However, some patients with AIDS-like symptoms are not HIV positive. This has led scientists to investigate alternate causes of AIDS-like symptoms in patients who are HIV negative.

Dr. Shyh-Ching Lo of the Armed Forces Institute of Pathology has found a novel pathogenic mycoplasma, *Mycoplasma fermentans* in patients with AIDS-like symptoms, some of whom were HIV negative. Although not all AIDS patients test positive for active mycoplasma, it is possible that the mycoplasma is in an inactive, hidden form in such patients. Some scientists have postulated that HIV is a largely benign viral infection which does not develop into AIDS unless there is also an infection with mycoplasma.

Dr. Lo isolated *M. fermentans* (then identified as Virus-Like Infectious Agents, or VLIA) from an AIDS patient and infected four silver leaf monkeys. All four died within 9 months and experienced symptoms similar to AIDS patients. Dr. Lo's research team could find no other pathogens that could have caused the monkeys' deaths. Shyh-Ching Lo, et al., *Fatal Infection of Silvered Leaf Monkeys with a Virus-Like Infectious Agent (VLIA) Derived From a Patient with AIDS*, Am. J. Trop. Med. Hyg., 40(4), pp. 399–409 (1989). Dr. Lo summarized medical research linking M. fermentans and AIDS in Mycoplasmas and AIDS in *Mycoplasmas: Molecular Biology and Pathogenesis* 525–545 (Jack Maniloff, et al., eds., American Society for Microbiology, 1992).

AIDS and CFS are both syndromes characterized by sustained and progressive illness. Patients can be chronically ill for years with symptoms that wax and wane, or, alternately, exhibit a steady progression toward disability or death. Many of the symptoms associated with CFS are also found in patients with AIDS. These include enlarged lymph nodes, musculoskeletal pain, headache, fatigue, weight loss, depression, and inability to concentrate. See Victor G. Daniels, AIDS 83–92 (MTP Press Limited 1987). In addition, AIDS and CFS patients are subject to opportunistic infections by many of the same viruses, such as Cytomegalovirus, Epstein-Barr virus, Herpes Simplex Virus, Non-A, Non-B Hepatitis (Hepatitis C), and Human T Cell Lymphotropic Viruses, types I and II (HTLV). Hepatitis C and HTLV are extremely rare in the North American heterosexual population. (Cowley, G., et al., supra, *A Debilitating Disease Afflicts Millions-And the Cause is Still a Mystery*, Newsweek, Nov. 12, 1990; Cowley, G., *AIDS or Chronic Fatigue?*, Newsweek, Sep. 7, 1992) This suggests that AIDS and CFS may share at least some similar immunosuppressive effects.

Historically, compositions derived from herbs have been used to treat a wide variety of diseases. Potent pharmacological substances have been identified in various herbal preparations, reflective of a pharmacological basis for their effects. The present invention is directed to a pharmaceutically effective composition derived from herbs which is useful in alleviating the symptoms associated with CFS and AIDS and to a method for so using these compositions.

SUMMARY OF THE INVENTION

The present invention particularly provides the following:

A pharmaceutical composition useful in reducing or alleviating the symptoms associated with Chronic Fatigue Syndrome or Acquired Immune Deficiency Syndrome in a patient exhibiting such symptoms, which comprises, addition to one or more optional pharmaceutically acceptable excipients, an extract containing herbs wherein said extract is prepared from the following herbs:

Chimaphila umbellate,
Apocynum androsaemifolium,
Symphytum officianale, and
Equisetum hyemale;

wherein the ratio of said herbs in parts by weight is about 6.0±1.2 to about 3.33±0.67 to about 4.75±1.0 to about 1±0.2, respectively.

The present invention is also directed to a specific composition (herein composition I) comprising about 1.991 g prince's pine, (Chimaphila umbellate); about 1.098 g bitterroot (Apocynum androsaeniifolium); about 1.560 g comfrey root (Symphytum officianale); and about 0.329 g horsetail (Equisetum hyemale). Composition I is prepared advantageous where the prince's pine, bitterroot and comfrey root are in the cut form and the horsetail is in the powdered form.

The invention is also directed to an extract prepared from composition I for oral administration. The extract from composition I is first prepared in about 10:3:3:1 volume ratio of herbs (i.e., in which the respective weights of the herbs is 1.991 g, 1.098 g, 1.560 g, and 0.329 g). Water at a temperature at or near its boiling point is then added to composition I to a final volume that is 98.0% by weight of the final composition or about 950 ml. The preparation is incubated at ambient temperature for approximately ten minutes and particulate material is removed, e.g., by straining or filtration. The resulting extract is a light to medium brown transparent liquid with the same viscosity as regular water, and is referred to herein as composition II-Unit Dose.

Composition II is conveniently prepared from composition II-Unit Dose by proportionately increasing each of the components used in composition II-Unit Dose in order to prepare compositions in the most economically efficient quantities.

In another aspect, the invention is directed to use of composition II in treating symptoms associated with CFS and AIDS. Composition II-Unit Dose is administered orally in liquid form at regular intervals, e.g., two to four times daily, until at least one of the symptoms associated with CFS or AIDS is reduced or eliminated. For example, one or two composition II-Unit Doses may be conveniently delivered three times a day before mealtime. The specific symptoms associated with CFS that may be alleviated by the method include fatigue, musculoskeletal pain, abnormal sleep patterns, headaches, blurred vision, dizziness, forgetfulness, excessive irritability, inability to concentrate, depression, low grade fever, pharyngitis, swollen lymph nodes and weight loss. The symptoms associated with AIDS that may be alleviated by the method include enlarged lymph nodes, musculoskeletal pain, headache, fatigue, weight loss, depression, and inability to concentrate. Most preferably, the one unit dose is administered 4 to 5 times a day. Optionally, the concomitant administration of dietary supplements of lecithin may be employed in quantities sufficient to reduce the dermatitis sometimes associated with the administration of composition II.

DETAILED DESCRIPTION OF THE INVENTION

The present invention is directed to an herbal-based extract useful in alleviating the symptoms associated with CFS and AIDS. Traditionally, the active ingredients in the extract have been recognized as having medicinal properties. For example, prince's pine is has been used to treat infections of the urinary tract, soft tissue, kidney and liver, as well as for gonorrhea, chronic rheumatitis and arthritis. Bitterroot is thought to promote the healing of mucus membranes, reduce pulse rate, treatment of nephritis, diabetes, and diseases of the skin and joints. Combined with prince's pine, bitterroot may exert antimicrobial effects *M. fermentans* infections associated, for example, with AIDS or CFS.

Comfrey root has been used in the treatment of cancer patients. It contains allantoin, alkaloids, and lithospermic acid, and is hypothesized to aid in the elimination of mycoplasmal grains from patients. Horsetail contains silica and has been used for kidney disease and parasitic diseases.

A. Preparation of the Composition II-Unit Dose

A unit dose composition of the present invention is made by first mixing the four above noted components as follows:

1. 1.991 g prince's pine (Chimaphila umbellate), preferably in cut form;
2. 1.098 g bitterroot (Apocynum androsaemifolium), preferably in cut form;
3. 1.560 g comfrey root (Symphytum officianale), preferably in cut form;
4. 0.329 g horsetail (Equisetum hyemale), preferably in powdered form;

The mixture of herbs described above can be used in the preparation of a composition suitable for oral administration. The herbs are placed in a measuring cup. Water heated to its boiling point is then added to the mixture to a final volume of 240 ml. The resulting suspension is covered and incubated, preferably for at least 10 minutes. Undissolved material is then removed, e.g., by straing, and the recovered fluid may then be administered to patients. In a most convenient embodiment patients can prepare the foregoing composition immediately before administration. However preparations may be prepared in advance and stored in an appropriate form, e.g., frozen or as a lyophilizate.

B. Alternative Means of Preparation

The preparation of composition for oral administration can be made more convenient by mixing a large amount of dry herbs in the relative proportions described above. The dry mixture can then be stored until use. The mixture may also be distributed in portions suitable for individual uses. One particularly convenient procedure is to distribute the dry mixture in process containers that can be incubated in heated water and then discarded. Thus the composition for oral administration could be prepared in a manner similar to the way in which commercial lyophilized coffee or tea beverages are typically made.

C. Solid Oral Dosage Form.

The lyophilized extract can be administered conveniently in solid oral dosage forms (tablets, capsules, soft gelatin capsules and the like) by combination with one or more pharmaceutically acceptable excipients followed by conventional techniques for finishing.

D. Use of the Composition in Treating Patients

The preferred liquid dosage for treating symptoms associated with CFS and AIDS is about 240 ml q.i.d., (960 ml total) per day. A patient should preferably ingest the composition before breakfast, at midday, before dinner and before bed. If desired, patients may take an extra fifth dose of 240 ml at about 3:00 a.m. It is preferred that patients should take the composition before eating.

Some individuals may find it desirable to begin with a lower dosage and gradually increase to 4 daily doses of 240 ml each. For example, patients may begin by taking 240 ml before breakfast, 60–90 ml before lunch, 60–90 ml before dinner, and 240 ml before bed. They may then increase the dosage to 240 ml before breakfast, 60–90 ml before lunch, 240 ml before dinner, and 240 ml before bed.

Administration should be continued until the patient's symptoms have been substantially reduced or eliminated. Symptoms associated with CFS that may be alleviated include fatigue, musculoskeletal pain, abnormal sleep patterns, headaches, blurred vision, dizziness, forgetfulness, excessive irritability, inability to concentrate, depression, low grade fever, pharyngitis, swollen lymph nodes and weight loss. The symptoms associated with AIDS that may be alleviated include enlarged lymph nodes, musculoskeletal pain, headache, fatigue, weight loss, depression, and inability to concentrate.

Upon administration of composition II-Unit Dose, a patient may feel drowsy. Some patients may feel a burning sensation, pain, or itching in their extremities, or experience headaches. These side effects subside as the patient recovers. Recovery may be gradual. The patient may slowly regain energy and look healthier. Typically a complete elimination of the fatigue and other symptoms associated with CFS or AIDS is accomplished within about nine months.

It is preferred that patients avoid foods with glucose, especially for the first two months of therapy. A patient may supplement his diet with soybean lecithin granules and extra water to reduce any side effects, e.g., dermatitis.

The compositions herein may be used with dietary supplements including: vitamin A, vitamin B complex with biotin, iron, vitamin C with bioflainoids, magnesium, selenium, zinc, copper, kelp, boron, one or two drops of liquid trace minerals, raw wheat germ (vitamin E), apple cider vinegar, Swiss cheese, and flax oil.

EXAMPLES

In order to examine the effectiveness of the composition in treating symptoms associated with AIDS and chronic fatigue syndrome ("CFS"), a survey was conducted of patients suffering from severe, and, in most cases, long-term symptoms. Patients were asked to sign a consent form in which they agreed to take two to four doses of the composition daily. After a period of several months, the patients were requested to prepare a report in which they noted any changes with respect to their symptoms. At the beginning of the survey, participants were also required to complete a survey form listing their symptoms and the time at which they first became ill.

A total of six patients participated in the study. Two of these had been diagnosed as having AIDS, two as having CFS, and two had not been diagnosed as having either condition but had a long history of experiencing the debilitating symptoms typically associated with CFS. Four of the patients took the composition for a period of three to five months before reporting effects. Two patients took the composition for a more extended period of time. A detailed description of the effects reported by each patient is contained below.

Case 1:

C.G. is a 41-year-old male who was diagnosed as having AIDS at the beginning of February 1996. At that time, he had a T-cell count of 63 per cubic millimeter and had symptoms that included extreme fatigue, daily low-grade fevers, sleep disorders, jaundice, and occasional mental confusion. He began taking the composition orally four or five times a day on Feb. 21, 1996. In addition, he took vitamin supplements and certain drugs prescribed by his physician (3TC, DDI, occasional antibiotics, and antidepressants). After three months on the composition, C.G. reported a marked reduction in the level and number of daily fevers, and a reduction in jaundice, sleeping problems, and fatigue. An analysis performed approximately one month after beginning on the composition indicated that his T-cell count had risen by 27%.

Case 2:

K. K. is a 25-year-old female living in Thailand who apparently contracted AIDS in April of 1990 and has experienced particularly severe symptoms during the last year and a half. The symptoms included back pain of such severity that K.K. was unable to move without serious pain for several days. On several occasions, the pain became so intense that she had to be rushed to a local hospital.

K.K. reported that she began to feel better immediately after beginning on the composition. After three months, her back pain had subsided.

Case 3:

L.D. is a female that was diagnosed as having CFS in 1988. She has had essentially continuous, flu-like symptoms since 1990. She experienced muscle pain, extreme weakness and fatigue, mental confusion, uncontrollable eye twitching, pain, weight loss, sleep disturbances, loss of both short- and long-term memory, and muscle spasms.

After four and a half months on the composition, L.D. reported an improvement in concentration, reduction in fatigue, an elimination of eye twitching, and a reduction in sleep disturbances.

Case 4:

C.B. is a female that was diagnosed as having CFS in February of 1994 after having symptoms since 1990. By August of 1993, she was confined mostly to her home due to incapacitating fatigue and muscle weakness. Other symptoms included painful lymph nodes, headaches, photophobia, eye twitching, memory loss, hypothermia, night sweats, insomnia, depression, and abdomial pain. After having taken the composition for 18 months, C.B. reported that all symptoms, with the exception of an occasional sore throat, had been eliminated.

Case 5:

R.G. is a male who has experienced the symptoms characteristic of CFS since February of 1993. Prior to beginning ingestion of the composition, he reported continuous and sometimes extreme pain that would incapacitate him for days at a time. He exhibited essentially continuous flu-like symptoms, including fevers, chills, and muscle aches. Other symptoms included sleep disturbances, extreme fatigue, shortness of breath, ear aches, dizziness, skin rashes, burning sensations, eye twitching, memory loss, weight loss, and night sweats.

After taking the composition orally over an extended period of time, R.G. reported an alleviation of virtually all of the above symptoms. For example, with regard to sleep disorders, the patient reported that, prior to taking the composition, he was typically unable to sleep for more than three hours at a time. After taking the composition, he was able to sleep for six hours with little disturbance. The pain that he had experienced prior to taking the composition has essentially disappeared and the other symptoms such as night sweats, flu-like symptoms, extreme fatigue and dizziness all occur with greatly reduced frequency and severity.

Case 6:

R.C. is a male whose health problems began in about 1985. About that time, he began to have difficulty in sleeping and to experience memory loss and difficulty in maintaining concentration. In addition, he experienced severe pain in his shoulders and neck, as well as weight fluctuations and flu-like symptoms. By 1991, he had lost two jobs because of mistakes resulting from an inability to concentrate and remember.

In late December of 1991, R.C. was diagnosed as having thyroid cancer, and he subsequently underwent a thyroidectomy and radiation therapy. By the summer of 1992, his oncologist informed him that he should no longer be experiencing symptoms due to the cancer. Nevertheless, his mental state continued to deteriorate, and by January of 1996 he was experiencing debilitating fatigue, flu-like symptoms, swollen lymph nodes, frequent headaches, severe muscle pain, blurred vision, cognitive difficulties, twitching eyes, hormonal problems, severe sleep disturbances, light sensitivity, dizziness, ear aches, breathing difficulties, night sweats, numbness in fingers and toes, skin rashes, and digestive problems.

R.C. began taking the composition orally in late Febmary of 1996. After four and one-half months, he reported that all of the symptoms described above were greatly diminished. His extreme fatigue had diminished to the point where he was able to work; he had only worked about five months in the previous four years. He reported that he was thinking much more clearly and that his sleep disturbances were greatly reduced.

What is claimed is:

1. A pharmaceutical composition useful in reducing or alleviating the symptoms associated with Chronic Fatigue Syndrome or Acquired Immune Deficiency Syndrome in a patient exhibiting such symptoms, which comprises, in addition to one or more optional pharmaceutically acceptable excipients an extract containing active ingredients, wherein said extract is prepared from the following herbs: *Chimaphila umbellate; Apocynum androsaemifolium; Symphytum officianale; and Equisetum hyemale* wherein the ratio of said herbs in parts by weight from which said extract is prepared, is about $6.0\pm1.2$ to about $3.33\pm0.67$ to about $4.75\pm1.0$ to about $1\pm0.2$, respectively.

2. The composition of claim 1, wherein said extract is prepared initially from the powdered form of Equisetum hyemale and from the cut form of *Chimaphila umbellate, Apocynum androsaemifolium, and Symphytum officianale.*

3. A method of preparing an oral pharmaceutical dosage form for oral administration comprising:
   (a) adding water to the powdered or cut form of the herbs of claim 1, wherein said water is at a temperature at or near its boiling point and is added to a final volume that is about 98.0% by weight of said composition;
   (b) incubating the resulting mixture; and
   (c) removing any undissolved material from the resulting incubate.

4. A pharmaceutically acceptable composition that is the product of the process of claim 3.

5. A method of reducing or alleviating one or more symptoms associated with Chronic Fatigue Syndrome (CFS) or Acquired Immune Deficiency Syndrome (AIDS) in a patient exhibiting such symptoms, which comprises administering to said patient an amount of the composition of claim 4 effective to reduce or eliminate at least one symptom of CFS or AIDS wherein said composition is administered at regular intervals until said symptom or symptoms are reduced or eliminated.

6. The method of claim 5, wherein said composition is administered at a dose of between about 60 and about 240 ml, 4 to 5 times a day.

* * * * *